(12) United States Patent
Strecter

(10) Patent No.: US 6,929,653 B2
(45) Date of Patent: Aug. 16, 2005

(54) APPARATUS AND METHOD FOR REPLACING AORTIC VALVE

(75) Inventor: Richard B. Strecter, Winchester, MA (US)

(73) Assignee: Medtronic, Inc., Minneapolis, MN (US)

(*) Notice: Subject to any disclaimer, the term of this patent is extended or adjusted under 35 U.S.C. 154(b) by 264 days.

(21) Appl. No.: 10/022,951

(22) Filed: Dec. 14, 2001

(65) Prior Publication Data

US 2002/0095116 A1 Jul. 18, 2002

Related U.S. Application Data

(60) Provisional application No. 60/256,196, filed on Dec. 15, 2000.

(51) Int. Cl.[7] ................................................. A61F 2/24
(52) U.S. Cl. ...................................... 606/200; 128/898
(58) Field of Search ........................... 606/200; 128/898

(56) References Cited

U.S. PATENT DOCUMENTS

| | | | |
|---|---|---|---|
| 3,671,979 A | 6/1972 | Moulopoulos | |
| 3,996,938 A | 12/1976 | Clark, III | |
| 4,056,854 A | 11/1977 | Boretos et al. | |
| 4,425,908 A | 1/1984 | Simon | |
| 4,527,549 A | 7/1985 | Gabbay | |
| 4,902,272 A | 2/1990 | Milder et al. | |
| 5,108,419 A | 4/1992 | Reger et al. | |

(Continued)

FOREIGN PATENT DOCUMENTS

| | | | |
|---|---|---|---|
| EP | 0408245 | 1/1991 | |
| WO | WO 99/15223 | 4/1999 | |
| WO | WO 99/33414 | 7/1999 | |
| WO | WO 00/44313 | * 8/2000 | ............. A61F/2/24 |
| WO | WO 00/47139 | 8/2000 | |

OTHER PUBLICATIONS

Antonatos PG, et al., Effect of the positioning of a balloon valve in the aorta on coronary flow during aortic regurgitation, J Thorac Cardiovasc Surg; Jul. 1984; 88(1): 128–33.

Antonatos PG, et al., Intraventricular Pumping At The Mitral Ring In Mitral Regurgitation; Life Support Syst; 1985; 3 Suppl 1:167–71.

Antonatos PG, et al., The Use Of A Small Intra–Aortic Balloon To Increase Coronary Flow; Life Support Syst; Jul.–Sep. 1983 1(3): 151–64.

Frederiksen J, et al. Use Of A Counterpulsation Balloon As A Substitute For The Pulmonic Valve: A New Application; Ann Thorac Surg; Jun. 1986; 41(6): 616–21.

Matsubara T, et al., Balloon Catheter With Check Valves For Experimental Relief Of Acute Aortic Regurgitation; Am Heart J; Oct. 1992; 124(4): 1002–8.

Moulopoulos SD, et al., Intra–Aortic Balloon Pump For Relief Of Aortic Regurgitation. Experimental Study, J Thorac Cardiovasc Surg; Jul. 1980:80(1):38–44.

Siwek LG, et al., Acute Control Of Pulmonary Regurgitation With A Balloon "Valve". An experimental investigation, J Thorac Cardiovasc Surg; Sep. 1985;90(3):404–9.

Cartwright RS, et al., Combined Replacement Of Aortic And Mitral Valves; J.A.M.A., Apr. 7, 1962;86–90.

*Primary Examiner*—Anhtuan T. Nguyen
*Assistant Examiner*—Bradford C Pantuck

(57) ABSTRACT

Apparatus and methods are disclosed for performing beating heart surgery. Apparatus is disclosed comprising a cannula having a proximal end and a distal end; an aortic filter in connection with the cannula, the aortic filter having a proximal side and a distal side; a check valve in connection with the cannula, the check valve disposed on the distal side of the aortic filter; and a coronary artery filter in connection with the cannula, the coronary artery filter having a proximal end and a distal end, and the distal end of the coronary artery filter extending distally away from the distal end of the cannula. A method is disclosed comprising providing apparatus for performing beating heart surgery; deploying the apparatus in an aorta; performing a procedure on the aortic valve; and removing the apparatus from the aorta.

13 Claims, 6 Drawing Sheets

U.S. PATENT DOCUMENTS

| | | | |
|---|---|---|---|
| 5,160,342 | A | 11/1992 | Reger et al. |
| 5,163,953 | A | 11/1992 | Vince |
| 5,254,097 | A | 10/1993 | Schock et al. |
| 5,300,086 | A | 4/1994 | Gory et al. |
| 5,324,304 | A | 6/1994 | Rasmussen |
| 5,329,942 | A | 7/1994 | Gunther et al. |
| 5,370,685 | A | 12/1994 | Stevens |
| 5,397,351 | A | 3/1995 | Pavcnik et al. |
| 5,411,552 | A | 5/1995 | Andersen et al. |
| 5,509,428 | A | 4/1996 | Dunlop |
| 5,545,214 | A | 8/1996 | Stevens |
| 5,549,626 | A | 8/1996 | Miller et al. |
| 5,549,665 | A | 8/1996 | Vesely et al. |
| 5,554,185 | A | 9/1996 | Block et al. |
| 5,571,215 | A | 11/1996 | Sterman et al. |
| 5,584,879 | A | 12/1996 | Reimold et al. |
| 5,607,465 | A | 3/1997 | Camilli |
| 5,682,906 | A | 11/1997 | Sterman et al. |
| 5,702,368 | A | 12/1997 | Stevens et al. |
| 5,713,951 | A | 2/1998 | Garrison et al. |
| 5,718,725 | A | 2/1998 | Sterman et al. |
| 5,728,153 | A | 3/1998 | Menkis et al. |
| 5,769,816 | A | 6/1998 | Barbut et al. |
| 5,797,960 | A | 8/1998 | Stevens et al. |
| 5,800,457 | A | 9/1998 | Gelbfish |
| 5,800,525 | A | 9/1998 | Bachinski et al. |
| 5,814,064 | A | 9/1998 | Daniel et al. |
| 5,814,097 | A | 9/1998 | Sterman et al. |
| 5,827,237 | A | 10/1998 | Macoviak et al. |
| 5,827,324 | A * | 10/1998 | Cassell et al. ............... 606/200 |
| 5,840,081 | A | 11/1998 | Andersen et al. |
| 5,848,964 | A | 12/1998 | Samuels |
| 5,855,597 | A | 1/1999 | Jayaraman |
| 5,855,601 | A | 1/1999 | Bessler et al. |
| 5,876,367 | A | 3/1999 | Kaganov et al. |
| 5,893,869 | A | 4/1999 | Barnhart et al. |
| 5,910,154 | A | 6/1999 | Tsugita et al. |
| 5,911,734 | A | 6/1999 | Tsugita et al. |
| 5,925,063 | A | 7/1999 | Khosravi |
| 5,928,261 | A | 7/1999 | Ruiz |
| 5,935,139 | A | 8/1999 | Bates |
| 5,941,896 | A | 8/1999 | Kerr |
| 5,947,995 | A | 9/1999 | Samuels |
| 5,954,741 | A | 9/1999 | Fox |
| 5,954,745 | A | 9/1999 | Gertler et al. |
| 5,957,949 | A | 9/1999 | Leonhardt et al. |
| 5,976,172 | A | 11/1999 | Homsma et al. |
| 5,980,555 | A | 11/1999 | Barbut et al. |
| 5,989,281 | A | 11/1999 | Barbut et al. |
| 6,168,579 | B1 | 1/2001 | Tsugita |
| 6,235,045 | B1 | 5/2001 | Barbut et al. |
| 6,258,120 | B1 | 7/2001 | McKenzie et al. |
| 6,309,399 | B1 | 10/2001 | Barbut et al. |
| 6,334,869 | B1 | 1/2002 | Leonhardt et al. |
| 6,371,970 | B1 | 4/2002 | Khosravi et al. |
| 6,375,670 | B1 * | 4/2002 | Greenhalgh ................. 606/200 |
| 6,395,014 | B1 | 5/2002 | Macoviak et al. |
| 6,692,513 | B2 * | 2/2004 | Streeter et al. ............. 606/200 |
| 2005/0015112 | A1 * | 1/2005 | Cohn et al. ................. 606/200 |

* cited by examiner

APPARATUS AND METHOD FOR REPLACING AORTIC VALVE

REFERENCE TO PENDING PRIOR PATENT APPLICATION

This patent application claims benefit of prior U.S. Provisional Patent Application Ser. No. 60/256,196, filed Dec. 15, 2000, now abandoned by Richard B. Streeter for APPARATUS AND METHOD FOR REPLACING AORTIC VALVE, which patent application is hereby incorporated herein by reference.

FIELD OF THE INVENTION

This invention relates to apparatus and methods for performing cardiac surgery in general, and more particularly to apparatus and methods for performing cardiac surgery while the heart is beating.

BACKGROUND OF THE INVENTION

In many cases, surgery must be performed on the heart. Under most circumstances, the heart is stopped while this surgery is performed, and the patient is kept alive during surgery through the use of a so-called "heart-lung machine". This type of surgery is frequently referred to as "on pump" surgery.

However, it has been recognized that the use of a heart-lung machine can have serious deleterious effects on the patient. Therefore, interest has become widespread in conducting so-called "off pump", or "beating heart", coronary artery bypass surgery. In this type of procedure, the bypass surgery is conducted while the patient's heart continues to beat. While this type of surgery can be significantly more difficult for the surgeon, the advantages can also be sufficiently great for the patient. As a result, a substantial percentage of bypass procedures are now done off pump.

However, for some types of procedures, e.g., aortic valve replacement, it can be effectively impossible to conduct the required surgery off pump using conventional apparatus and methods.

However, in pending PCT Patent Application No. PCT/US00/02126, filed Jan. 27, 2000 by Viacor Incorporated for CARDIAC VALVE PROCEDURE METHODS AND DEVICES, which patent application is hereby incorporated herein by reference, there is disclosed a novel apparatus and method for conducting off pump aortic valve replacement. In this patent application there is disclosed, among other things, apparatus comprising a temporary valve and filter which is placed in the aorta downstream from the defective aortic valve and which can effectively replace the functionality of the defective aortic valve while that valve is resected and replaced, and which also prevents debris from the valve resection from passing downstream during the resection procedure.

One object of the present invention is to provide a novel apparatus and method for providing improved protection for the coronary arteries during valve resection.

Another object of the present invention is to provide a novel apparatus and method for providing improved coronary perfusion during valve resection.

Another object of the present invention is to provide, in a single apparatus, used through a single point of entry, (1) a check valve for ensuring unidirectional flow of blood from the heart to the circulatory system, (2) filtration mechanisms for preventing debris from passing down the coronary arteries and/or the aorta, (3) apparatus to augment coronary perfusion, and (4) apparatus for passing instruments from the incision site to the heart.

SUMMARY OF THE INVENTION

These and other objects are achieved through the provision and use of novel apparatus which, in one preferred form of the invention, comprises a cannula; an aortic filter connected to the cannula; a check valve connected to the cannula distally of the aortic filter; and a coronary artery filter connected to the cannula and extending distally of the check valve. During use, the apparatus is deployed in the aorta so that the coronary artery filter covers the openings (coronary ostia) of the coronary arteries, the check valve is deployed downstream from the coronary artery filter, and the aortic filter is deployed downstream from the check valve. Among other things, in addition to delivering the aortic filter, check valve and coronary artery filter to the surgical site and supporting them there, the cannula also permits the delivery of instruments to the surgical site.

In another preferred embodiment, the device further comprises one or more passageways for perfusing the coronary arteries with filtered blood, especially during diastole.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like elements and further wherein.

DETAILED DESCRIPTION OF THE PREFERRED EMBODIMENTS

All configurations of the present invention are generally believed to require a seal between the apparatus and the blood flow path to ensure all blood is filtered during systole and the blood flow is blocked during diastole for apparatus configurations that include a temporary check valve to replace the function of the aortic valve. During systole, the seal against the periphery of the aortic valve need not hold back much pressure since the check valve provides very little resistance to blood flow and debris tends to follow laminar flow through the device and valve. During diastole, the check valve closes and the seal between the device and the blood flow path must hold back the diastolic pressure. Blood leaking through the device during diastole is called peri-valvular leakage and blood leaking around the device is called peri-prosthetic leakage. The present invention provides several configurations for sealing during systole and diastole.

Figure 1:
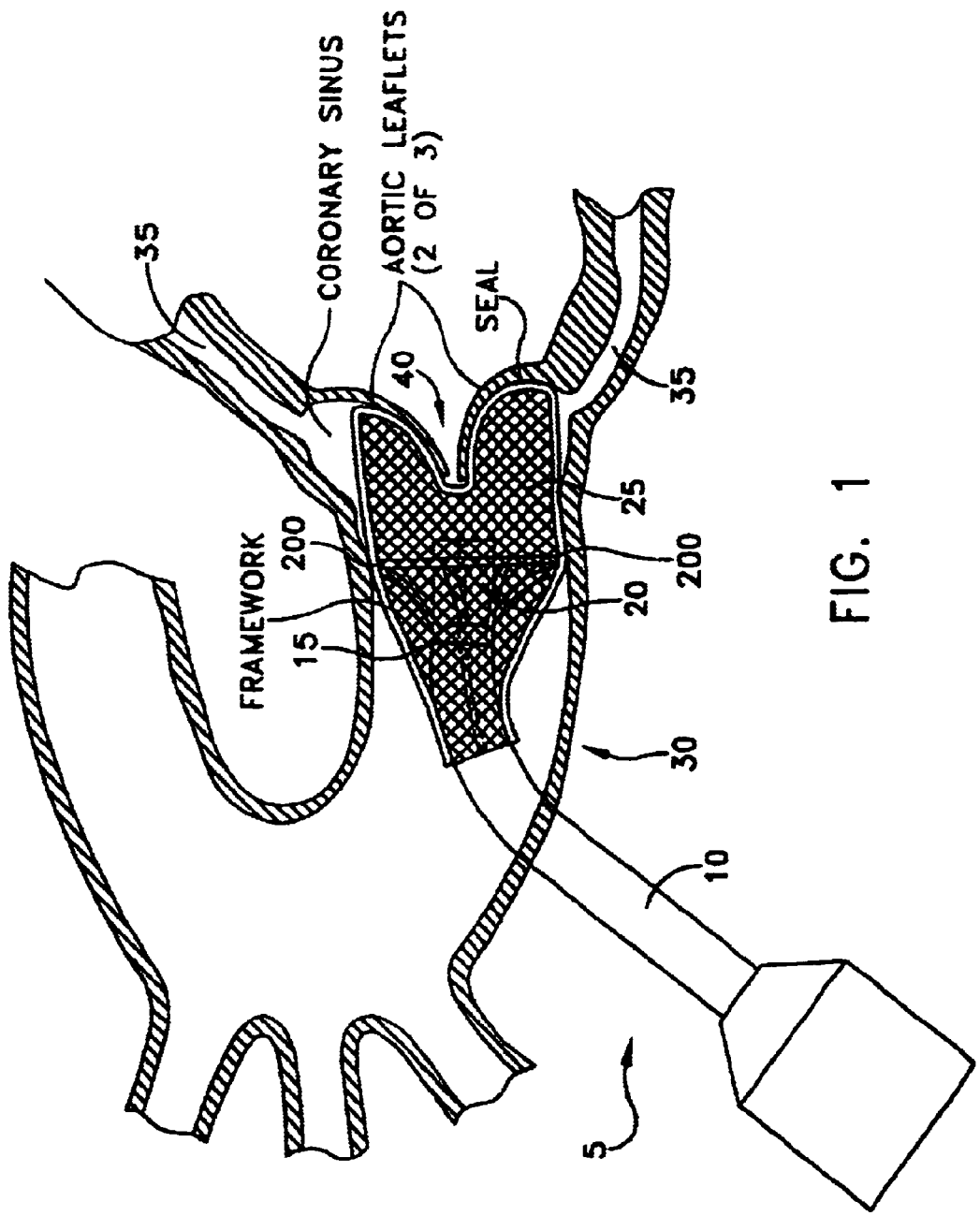
FIG. 1 is a schematic drawing showing a first embodiment of the present invention deployed adjacent to the aortic valve of the heart.

Looking first at FIG. 1, there is shown an apparatus 5 which comprises a first preferred embodiment of the present invention. Apparatus 5 generally comprises a cannula 10; an aortic filter 15 connected to cannula 10; a check valve 20 connected to cannula 10 distally of aortic filter 15; and a coronary artery filter 25 connected to the cannula and extending distally of check valve 20. Among other things, in addition to delivering the aortic filter, check valve and coronary artery filter to the surgical site and supporting them there, the cannula also permits the delivery of instruments to the surgical site. If desired, coronary artery filter 25 may have a different porosity than aortic filter 15. By way of example but not limitation, coronary artery filter 25 may have a larger mesh size than aortic filter 15. Apparatus 5 is configured so that it will make a substantial seal with aorta 30 at 200.

During use, apparatus 5 is deployed in aorta 30 so that coronary artery filter 25 covers the openings of the coronary arteries 35 and seals against the periphery of the aortic valve, check valve 20 is deployed downstream from coronary artery filter 25, and aortic filter 15 is deployed downstream from check valve 20. As a result of this construction, during systole, blood can pass into the aorta, past check valve 20 and past aortic filter 15. Correspondingly, during diastole, blood will be prevented from passing back through check valve 20. Furthermore, aortic valve 40 may be safely resected with apparatus 5 in place, since (i) during systole, aortic filter 15 will prevent debris from the resection from passing down aorta 30, and (ii) during systole or diastole, coronary artery filter 25 will prevent debris from passing down coronary arteries 35.

Figure 2:
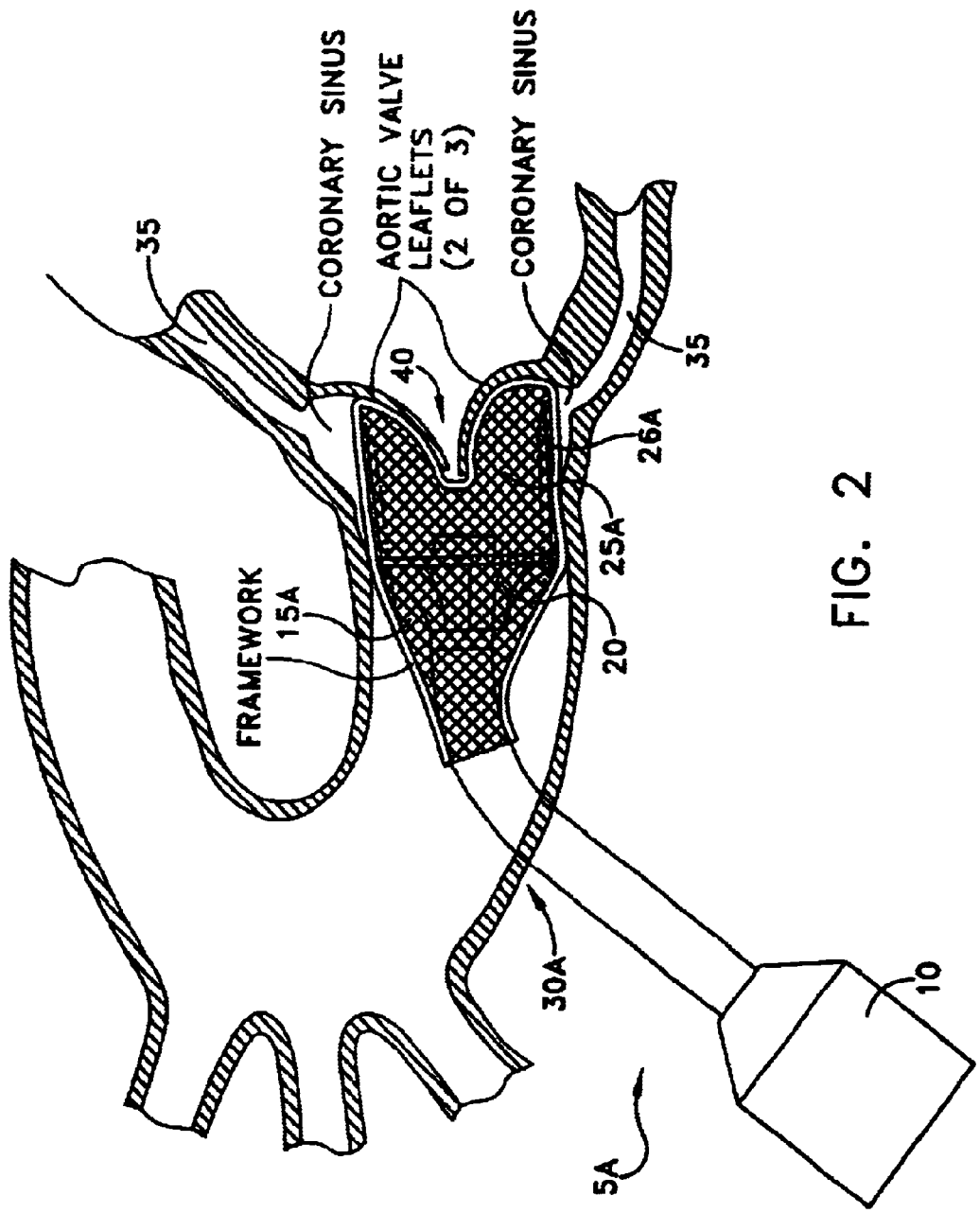
FIG. 2 is a schematic drawing showing a second embodiment of the present invention deployed adjacent to the aortic valve of the heart.
Figure 2A:
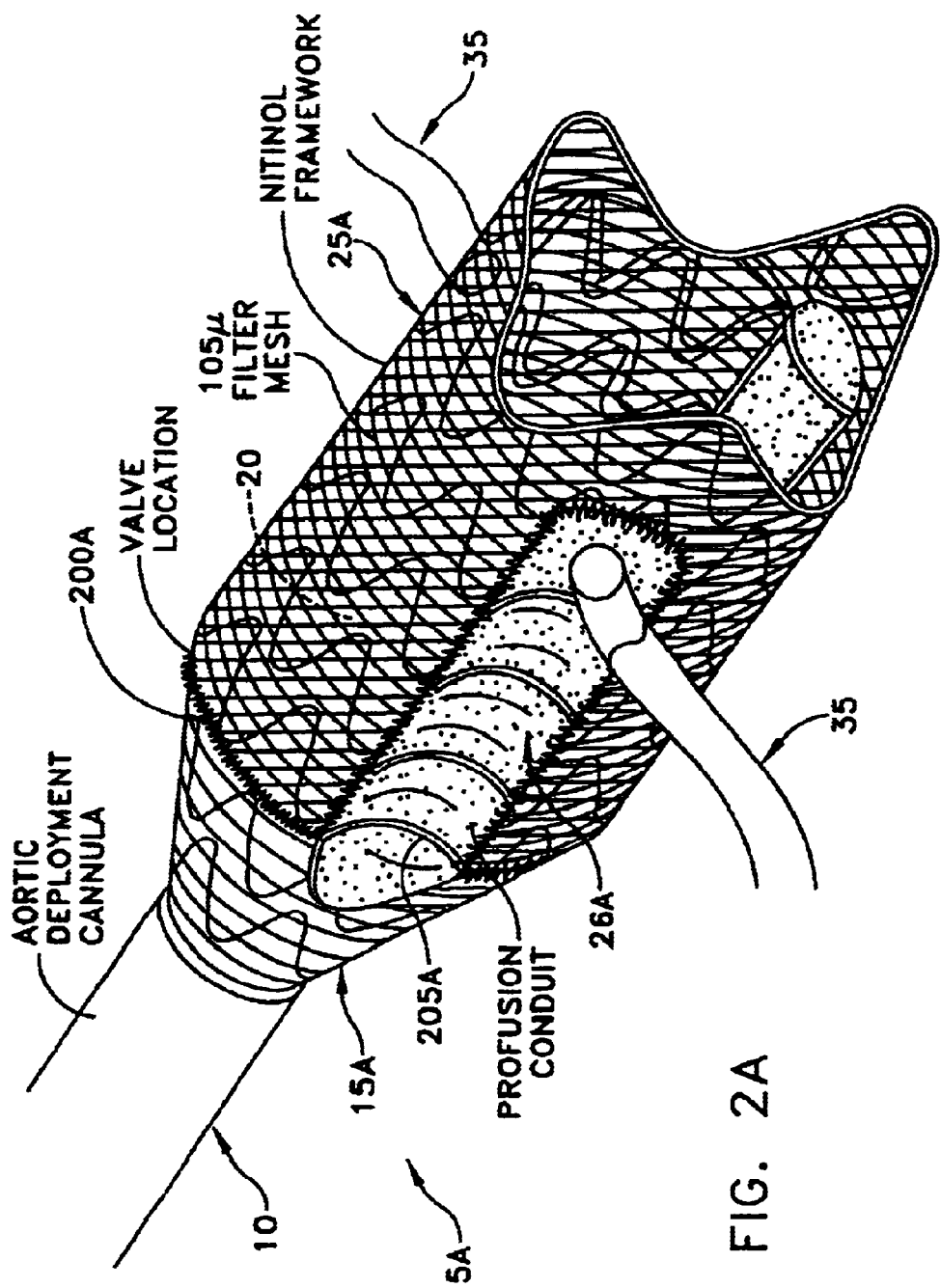
FIG. 2A is a schematic drawing showing details of the apparatus shown in FIG. 2.

Looking next at FIGS. 2 and 2A, there is shown an apparatus 5A which comprises a second preferred embodiment of the invention. Apparatus 5A generally comprises a cannula 10; an aortic filter 15A connected to cannula 10; a check valve 20 connected to cannula 10 distally of aortic filter 15A; and a coronary artery filter 25A connected to the cannula and extending distally of check valve 20. Among other things, in addition to delivering the aortic filter, check valve and coronary artery filter to the surgical site and supporting them there, the cannula also permits the delivery of instruments to the surgical site. If desired, coronary artery filter 25A may have a different porosity than aortic filter 15A. By way of example but not limitation, coronary artery filter 25A may have a larger mesh size than aortic filter 15A. In addition to the foregoing, coronary artery filter 25A includes a plurality of impermeable membranes 26A extending longitudinally along coronary artery filter 25A. The proximal ends of impermeable membranes 26A are located adjacent to the upstream side of aortic filter 15A. Impermeable membranes 26A serve as liners to channel blood flow to coronary arteries 35 during diastole, as will hereinafter be discussed in further detail. Apparatus 5A is configured so that it will make a substantial seal with aorta 30 about the perimeter of check valve 20, except for the portion of the perimeter adjacent to impermeable membranes 26A. In other words, apparatus 5A is configured so that it will make a substantial seal with aorta 30 at 200A in FIG. 2A, but not at 205A in FIG. 2A.

During use, apparatus 5A is deployed in aorta 30 so that the impermeable membranes 26A of coronary artery filter 25A are aligned with, and substantially cover, the openings of the coronary arteries 35 and seals against the periphery of the aortic valve, check valve 20 is deployed downstream from coronary artery filter 25A, and aortic filter 15A is deployed downstream from check valve 20. As a result of this construction, during systole, blood can pass into the aorta, past check valve 20 and past aortic filter 15A. Correspondingly, during diastole, blood will be prevented from passing back through check valve 20. However, blood will be able to pass around check valve 20 by following the channels or passageways defined by impermeable membranes 26A, so that the coronary arteries will be perfused during diastole. Furthermore, aortic valve 40 may be safely resected with apparatus 5A in place, since (i) during systole, aortic filter 15A will prevent debris from the resection from passing down aorta 30, and (ii) during diastole, only blood already having passed through aortic filter 15A will be able to pass down coronary arteries 35.

Figure 3:
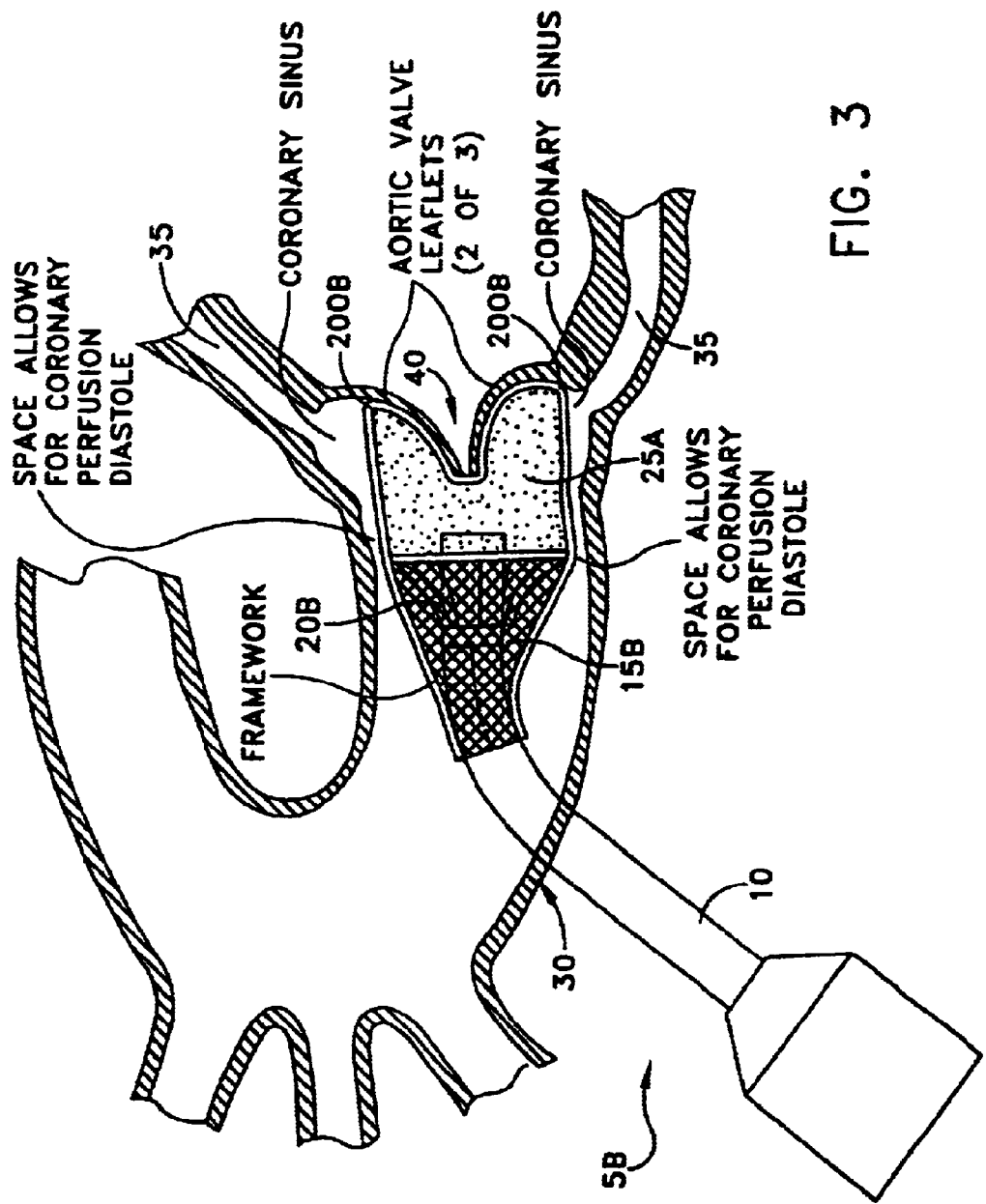
FIG. 3 is a schematic drawing showing a third embodiment of the present invention deployed adjacent to the aortic valve of the heart.

Looking next at FIG. 3, there is shown an apparatus 5B which comprises a third preferred embodiment of the invention. Apparatus 5B generally comprises a cannula 10; an aortic filter 15B connected to cannula 10; a check valve 20B connected to cannula 10 distally of aortic filter 15B; and an impermeable membrane 25B connected to the cannula and extending distally of check valve 20B. Among other things, in addition to delivering the aortic filter, check valve and impermeable membrane to the surgical site and supporting them there, the cannula also permits the delivery of instruments to the surgical site. Aortic filter 15B, check valve 20B and impermeable membrane 25B are all adapted to be spaced, along at least some portion of their circumference, from the surrounding wall of aorta 30, whereby to define one or more passageway(s) alongside the apparatus. In addition, impermeable membrane 25B is adapted to make a sealing engagement with the periphery of aortic valve 40, i.e., at 200B in FIG. 3.

During use, apparatus 5B is deployed in aorta 30 so that impermeable membrane 25B engages the periphery of aortic valve 40, check valve 20B is deployed downstream from impermeable membrane 25B, and aortic filter 15B is deployed downstream from check valve 20B. As a result of this construction, during systole, blood can pass into the aorta, past check valve 20B and past aortic filter 15B. Correspondingly, during diastole, blood will be prevented from passing back through check valve 20B into the heart, but it will be able to pass back to coronary arteries 35 through the aforementioned peripheral passageway(s) established between apparatus 5B and the wall of the aorta. Furthermore, aortic valve 40 may be safely resected with apparatus 5B in place, since (i) during systole, aortic filter 15B will prevent debris from the resection from passing down aorta 30, and (ii) during diastole, only blood having already passed through aortic filter 15B will be able to pass down coronary arteries 35.

Figure 4:
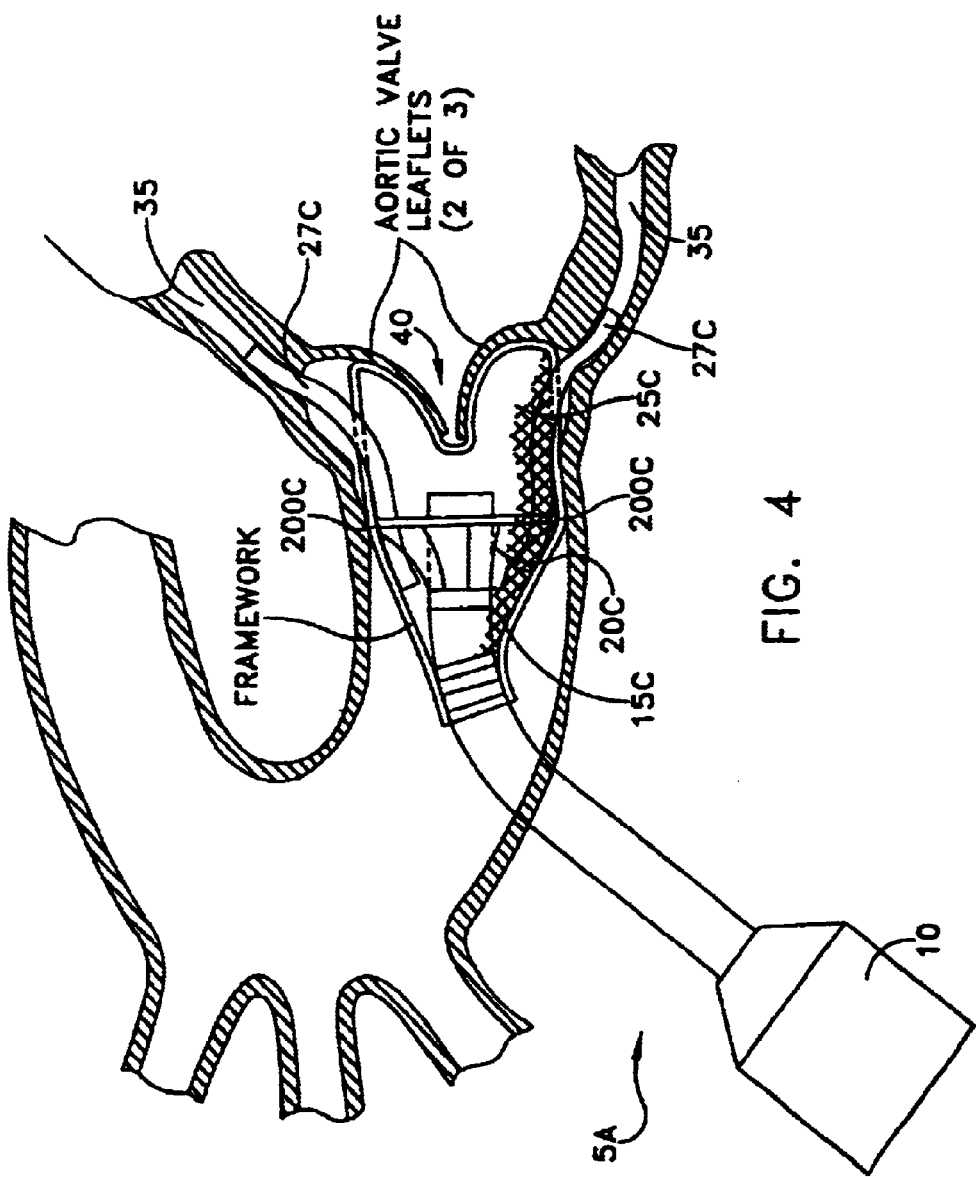
FIG. 4 is a schematic drawing showing a fourth embodiment of the present invention deployed adjacent to the aortic valve of the heart.

Looking next at FIG. 4, there is shown an apparatus 5C which comprises a fourth preferred embodiment of the invention. Apparatus 5C generally comprises a cannula 10; an aortic filter 15C connected to cannula 10; a check valve 20C connected to cannula 10 distally of aortic filter 15C; and a coronary artery filter 25C connected to the cannula and extending distally of check valve 20C. Among other things, in addition to delivering the aortic filter, check valve and coronary artery filter to the surgical site and supporting them there, the cannula also permits the delivery of instruments to the surgical site. If desired, coronary artery filter 25C may have a different porosity than aortic filter 15C. By way of example but not limitation, coronary artery filter 25C may have a larger mesh size than aortic filter 15C. In addition to the foregoing, a plurality of conduits 27C, formed of impermeable tubular material, are attached downstream of the check valve 20C and extend, distally, parallel to coronary artery filter 25C. Apparatus 5C is configured so that it will make a substantial seal with aorta 30 at 200C.

During use, apparatus 5C is deployed in aorta 30 so that the free ends of conduits 27C are disposed in the coronary arteries 35, possibly by a guided catheter, a guidewire or other delivery mechanism, and coronary artery filter 25C otherwise covers the openings of the coronary arteries 35, check valve 20C is deployed downstream from coronary artery filter 25C, and aortic filter 15C is deployed downstream from check valve 20C. As a result of this construction, during systole, blood can pass into the aorta, past check valve 20C and past aortic filter 15C.

Correspondingly, during diastole, blood will be prevented from passing back through check valve 20C. However, blood will be able to pass around check valve 20C by following conduits 27C so that the coronary arteries will be perfused with blood during diastole. Furthermore, aortic valve 40 may be safely resected with apparatus 5C in place, since (i) during systole, aortic filter 15C will prevent debris from the resection from passing down aorta 30, and (ii) during diastole, only blood already having passed through aortic filter 15C will be able to pass down coronary arteries 35.

Figure 5:
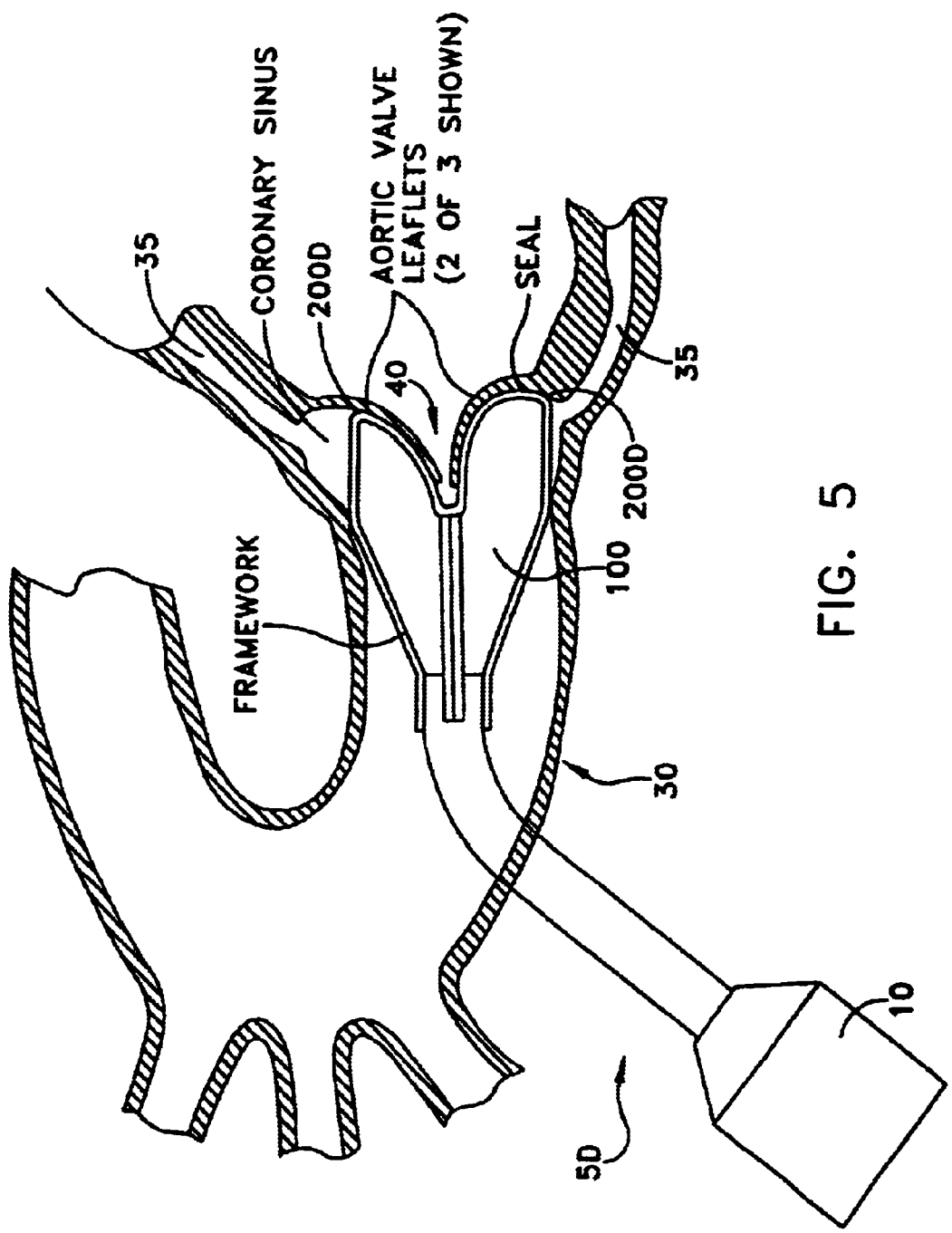
FIG. 5 is a schematic drawing showing a fifth embodiment of the present invention deployed adjacent to the aortic valve of the heart.

Looking next at FIG. 5, there is shown an apparatus 5D which comprises another preferred embodiment of the present invention. Apparatus 5D comprises a cannula 10 and a filter 100 connected to the cannula and extending distally of the cannula. Among other things, in addition to delivering filter 100 to the surgical site and supporting it there, the cannula also permits the delivery of instruments to the surgical site. Filter 100 is adapted to make a sealing engagement with the periphery of aertic valve 40, i.e., at 200D in FIG. 5.

During use, apparatus 5D is deployed in aorta 30 so that filter 100 covers the aorta and the openings (coronary ostia) of the coronary arteries 35. As a result of this construction, during systole, blood will pass through filter 100 before passing down the aorta and/or down the coronary arteries. During diastole, blood will pass through filter 100 before passing down the coronary arteries.

What is claimed is:

1. Apparatus for performing beating heart surgery, said apparatus comprising:
    a cannula having a proximal end and a distal end, the distal end of said cannula configured for deployment substantially concentrically in an aorta to allow blood flow during systole in a direction proximally from the distal end to the proximal end of said cannula;
    an aortic filter mounted on a distal end portion of said cannula for disposition in the aorta;
    a check valve mounted on the distal end portion of said cannula and disposed distally of said aortic filter mounted on the distal end portion of said cannula; and
    a coronary artery filter connected to said cannula and extending distally of said check valve, a distal portion of said coronary artery filter being configured for deployment upstream of said aortic filter check valve, and said coronary artery filter being configured to make a sealing engagement with a periphery of an aortic valve and cover openings into coronary arteries.

2. Apparatus according to claim 1 wherein said cannula permits delivery of an instrument to a surgical site.

3. Apparatus according to claim 1 wherein the porosity of said coronary artery filter is different from the porosity of said aortic filter.

4. Apparatus according to claim 1 wherein said coronary artery filter has a larger mesh size than said aortic filter.

5. Apparatus according to claim 1 wherein said apparatus is configurable to form a substantial seal with a vascular structure.

6. Apparatus according to claim 5 wherein the vascular structure is an inner surface of an aorta.

7. Apparatus according to claim 1 further comprising at least one impermeable membrane extending longitudinally along a surface of said coronary artery filter.

8. Apparatus according to claim 7 wherein said at least one impermeable membrane is provided with a proximal end and a distal end in an orientation corresponding to the proximal end of said cannula and the distal end of said cannula, respectively, and the proximal end of said at least one impermeable membrane is connected to said coronary artery filter so as to channel blood flow to a coronary artery during diastole.

9. Apparatus according to claim 1 wherein said coronary artery filter forms a perfusion conduit on a surface thereof so as to allow blood flow to a coronary artery during diastole.

10. Apparatus according to claim 9 further comprising an impermeable membrane extending longitudinally along a surface of said coronary artery filter, said impermeable membrane having a proximal end and a distal end in an orientation corresponding to the proximal end of said cannula and the distal end of said cannula, respectively, and the proximal end of said impermeable membrane is connected to said coronary artery filter so as to channel blood flow to the coronary arteries during diastole.

11. Apparatus according to claim 10 wherein said apparatus is configurable to form a substantial seal with an aorta, with an outer surface of said coronary artery filter leaving the perfusion conduit unobstructed.

12. A method for performing beating heart surgery, said method comprising:
    providing apparatus comprising:
        a cannula having a proximal end and a distal end, the distal end of said cannula configured for deployment substantially concentrically in an aorta to allow blood flow during systole in a direction proximally from the distal end to the proximal end of the cannula;
        an aortic filter mounted on a distal end portion of the cannula for disposition in the aorta;
        a check valve mounted on the distal end portion of said cannula and disposed distally of the aortic filter mounted on the distal end portion of said cannula; and
        a coronary artery filter connected to the cannula, and extending distally of the check valve, a distal portion of the coronary artery filter being configured for deployment upstream of the aortic filter, and extending distally from the distal end of the cannula, the coronary artery filter being configured to cover openings into coronary arteries adjacent a periphery of an aortic valve;
    deploying the apparatus in an aorta;
    performing a procedure on the aortic valve; and
    removing the apparatus from the aorta.

13. A method for performing beating heart surgery, said method comprising:
    providing apparatus comprising:
        a cannula having a proximal end and a distal end, the distal end of said cannula being configured for deployment substantially concentrically in an aorta to allow blood flow during systole in a direction proximally from the distal end to the proximal end thereof; and
        a filter mounted on a distal portion of the cannula, the filter having a proximal end and a distal end, the distal end of the filter extending in a direction away from the distal end of the cannula;
        wherein the filter is adapted to make a sealing engagement with a periphery of an aortic valve, and is adapted to cover openings extending into coronary arteries;
    deploying the apparatus in an aorta;
    performing a procedure on the aortic valve; and
    removing said apparatus from the aorta.

* * * * *